US010253055B2

(12) United States Patent
Stephan et al.

(10) Patent No.: US 10,253,055 B2
(45) Date of Patent: Apr. 9, 2019

(54) RUTHENIUM-BASED TRIAZOLE CARBENE COMPLEXES

(71) Applicant: THE GOVERNING COUNCIL OF THE UNIVERSITY OF TORONTO, Toronto (CA)

(72) Inventors: Douglas Wade Stephan, Toronto (CA); Bidraha Bagh, Toronto (CA); Adam McKinty, Alberta (CA)

(73) Assignee: THE GOVERNING COUNCIL OF THE UNIVERSITY OF TORONTO, Toronto, Ontario (CA)

( * ) Notice: Subject to any disclaimer, the term of this patent is extended or adjusted under 35 U.S.C. 154(b) by 0 days.

(21) Appl. No.: 15/306,530

(22) PCT Filed: Apr. 23, 2015

(86) PCT No.: PCT/CA2015/050340
§ 371 (c)(1),
(2) Date: Oct. 25, 2016

(87) PCT Pub. No.: WO2015/161383
PCT Pub. Date: Oct. 29, 2015

(65) Prior Publication Data
US 2017/0044195 A1 Feb. 16, 2017

(30) Foreign Application Priority Data

Apr. 25, 2014 (EP) ...................................... 14166024

(51) Int. Cl.
| | | |
|---|---|---|
| *C07F 15/00* | (2006.01) |
| *B01J 31/18* | (2006.01) |
| *C07D 233/58* | (2006.01) |
| *C07C 209/70* | (2006.01) |
| *C07C 5/03* | (2006.01) |
| *C07C 253/30* | (2006.01) |
| *C08C 19/02* | (2006.01) |
| *C07C 45/62* | (2006.01) |
| *B01J 31/16* | (2006.01) |
| *C08F 236/12* | (2006.01) |
| *C07C 5/08* | (2006.01) |
| *B01J 31/22* | (2006.01) |
| *C07C 5/10* | (2006.01) |
| *C07D 249/06* | (2006.01) |

(52) U.S. Cl.
CPC .......... *C07F 15/0046* (2013.01); *B01J 31/16* (2013.01); *B01J 31/2273* (2013.01); *B01J 31/2295* (2013.01); *C07C 5/03* (2013.01); *C07C 5/08* (2013.01); *C07C 5/10* (2013.01); *C07C 45/62* (2013.01); *C07C 209/70* (2013.01); *C07C 253/30* (2013.01); *C07D 233/58* (2013.01); *C08C 19/02* (2013.01); *C08F 236/12* (2013.01); *B01J 2231/645* (2013.01); *B01J 2531/821* (2013.01); *C07C 2531/22* (2013.01); *C07C 2531/24* (2013.01); *C07C 2601/14* (2017.05); *C07D 249/06* (2013.01)

(58) Field of Classification Search
CPC ............... C07F 15/0046; B01J 31/2273; B01J 31/2295; B01J 31/1805; B01J 31/1845; B01J 2531/821; C08C 19/02; C08F 236/12; C07D 249/06
See application file for complete search history.

(56) References Cited

PUBLICATIONS

Ogata et al., Dalton Transactions 42 (2013) 2362-2365.*
Bhattacharjee, Susmita, et. al., "High-pressure Hydrogenation of Nitrile Rubber: Thermodynamics and Kinetics", Ind. Eng. Chem. Res. 1991, 30, American Chemical Society, pp. 1086-1092.
Hallman, P.S., et al., "Selective Catalytic Homogeneous Hydrogenation of Terminal Olefins using Tria (triphenylphosphine)hydridochlororuthenium(11; Hydrogen Transfer in Exchange and Isomerisation Reactions of Olefins", Chem. Comm. 7,1967, pp. 305-306, Abstract.
Belger, Christian, et al., "A Selective Ru-Catalyzed Semireduction of Alkynes to Z Olefins under Transfer-Hydrogenation Conditions", Chem. Eur. J. 2010, 16, Wiley-VCH Verlag GmbH & Co., pp. 12214-12220.
Chantler, Victoria L., et al., "Stoichiometric and catalytic reactivity of the N-heterocyclic carbene ruthenium hydride complexes . . . ", Dalton Trans. Issue 19, 2008, The Royal Society of Chemistry, pp. 2603-2614, Abstract.
Chatwin, Sarah L., et al., "H-X Bond Activation via Hydrogen Transfer to Hydride in Ruthenium N-Heterocyclic Carbene Complexes: Density functional and Synthetic Studies", Organometallics 2006, 25, American Chemical Society, pp. 99-110.
Beach, Nicholas J., et al., "Hydrogenolysis versus Methanolysis of First- and Second-Generation Grubbs Catalysts: Rates, Speciation, and Implications for Tandem Catalysis", Organometallics, 2010, 29, American Chemical Society, pp. 5450-5455.
Rashid-Abdur, Kamaluddin, et al., "Coordinatively Unsaturated Hydridoruthenium(II) Complexes of N-Heterocyclic Carbenes", Organometallics 2004, 23, American Chemical Society, pp. 86-94.
Ogata, Kenichi, et al., "Position-selective intramolecular aromatic C-H bond activation of 1,2,3-triazol-5-ylidene (txNHC) ligands in (p-cymene_ruthenium(II) complexes", Dalton Trans., 2013, 42, The Royal Society of Chemistry, pp. 2362-2365.
Petronilho, Ana, et al., "Photolytic water oxidation catalyzed by a molecular carbene iridium complex", Dalton Trans., 2012, 41, The Royal Society of Chemistry, pp. 13074-13080.

(Continued)

*Primary Examiner* — Roberto Rabago
(74) *Attorney, Agent, or Firm* — Norris McLaughlin, PA (57) ABSTRACT

The present invention relates to novel ruthenium-based triazole carbene complexes comprising specific ligands, their preparation and their use as catalysts in hydrogenation processes. Such complex catalysts are inexpensive, thermally robust, gel formation inhibiting and olefin selective.

20 Claims, 2 Drawing Sheets

(56) References Cited

PUBLICATIONS

Lalrempuia, Ralte, et al, "Water Oxidation Catalyzed by Strong Carbene-Type Donor-Ligand Complexes of Iridium", Angew. Chem. Int. Ed. 2010, 49, Wiley-VCH Verlag GmbH & Co., pp. 9765-9768.
Saravanakumar, Rajendran et al., "Synthesis and Structure of 1,4-Diphenyl-3-methyl-1,2,3-triazol-5-ylidene Palladium Complexes and Application in Catalytic Hydroarylation of Alkynes", Organometallics 2011, 30, American Chemical Society, pp. 1689-1694.
Viciano, Monica, et al., "Aliphatic versus Aromatic C-H Activation in the Formation of Abnormal Carbenes with Iridium: A Combined Experimental and Theoretical Study", Organometallics, 2007, 26, American Chemical Society, pp. 5304-5314.
Houben-Weyl, Methoden der Organischen Chemie Bd.14/1, 30, 1961, Georg Thieme Verlag, abstract.
Guo, Xiangyao et al., "Catalytic Hydrosilylation of Diene-Based, Polymers, Hydrosilylation of Styrene-Butadiene Copolymer and Nitrile-butadiene Copolymer", Macromolecules 1992, 25, American Chemical Society, pp. 883-886.
Mao, Tian-Fu, et al., "Catalytic hydrogenation of nitrile-butadiene copolymers by cationic rhodium complexes", J. Mol. Catal. A:Chem. 1998, 135, Elsevier Science B.V., pp. 121-132.
McManus, N.T., et al., Improvements in the Hydrogenation of Nitrile Rubber using Wilkinson's Catalyst, Rubber Chem. and Technol. 2008, 81, American Chemical Society, pp. 227-243, Abstract.
Chatwin, Sarah L., et al., Reactivity of the N-heterocyclic carbone complexes [Ru(IMes)2 (Co)HX] (X=OH, Cl) with alkynes, Inorganica Chimica Acta, vol. 363, Issue 3, 2010, Elsevier, pp. 625-632, abstract.
Jardine, I., et al., "Homogeneous and Hetergeneous Hydrogenation", Tetrahedron Lett. No. 40, 1966, Pergamon Press Ltd., pp. 4871-4875.
Balaraman, Ekambaram, et al., "Direct Hydrogenation of Amides to Alcohols and Amines under Mild Conditions", J. Am. Chem. Soc. 2010, 132, American Chemical Society, pp. 16756-16758.
Vaska, L., et al., "Complex Carbonyl Hydrides of Osmium and Ruthenium", Communications to the Editor, J. Am. Chem. Soc. 1961, 83, American Chemical Society, pp. 1262-1263.
Joseph, Trissa, et al., "Hydrogenation of olefins over hydrido chlorocarbonyl tris-(triphenylphosphine) rutheniumj(II) complex immobilized on functionalized MCM-41 and SBA-15", J. Molecular Catalysis A: Chemical 206 (2003), Elxevier B.V., pp. 13-21.
Lee, John P., et al., "Six-, Five-, and Four-Coodinate Ruthenium(II) Hydride Complexes Supported by N-Heterocyclic Carbene Ligands: Snythesis, Characterization, Fundamental Reactivity, and Catalytic Hydrogenation of Olefins, Aldehydes, and Ketones", Organometallics 2009, 28, American Chemical Society, pp. 1758-1775.
Lovell, Peter A., et al., "Emulsion Polymerization and Emulsion Polymers", 1997, Wiley, abstract.
Bagh, Bidraha, et al., "Half sandwich ruthenium(II) hydrides hydrogenation of terminal, internal, cyclic and functionalized olefins", Dalton Transactions, Issue 41, 2014, The Royal Society of Chemistry, pp. 15638-15645, abstract.
Bagh, Bidraha, et al., "i1,2,3-Triazolylidene Ruthenium(II)-Cyclometalated Complexes and Olefin Selective Hydrogenation Catalysis", Dalton Transactions, vol. 44, 2014, The Royal Society of Chemistry, pp. 2712-2723.
Delgado-Rebollo, Manuela, et al., "Synthesis and catalytic alcohol oxidation and ketone transfer hydrogenation activity of donor-functionliazed mesoionic triazolylidene ruthenium(II) complexes", Dalton Transactions, 2014, 43, The Royal Society of Chemistray, pp. 4462-4473.
Baratta, Walter, et al., "Fast transfer hydrogenation using a highly active orthometalated heterocyclic carbene ruthenium catalyst", J. Organometallic Chem 690, 2005, Elsevier B.V., pp. 5570-5575.
International Search Report from corresponding International Application No. PCT/CA2015/050340, dated Jul. 13, 2015, one page.
European Search Report from corresponding European Application No. 14166024, dated Sep. 5, 2014, one page.

\* cited by examiner

Figure 1

FT-IR spectrum of the Perbunan® 3435 before hydrogenation.

Figure 2

FT-IR spectrum of the polymer after hydrogenation (Compound 1, 2.5 μmol).

Figure 3

FT-IR spectrum of the polymer after hydrogenation (Compound 6, 2.5 μmol).

RUTHENIUM-BASED TRIAZOLE CARBENE COMPLEXES

FIELD OF THE INVENTION

The present invention relates to novel ruthenium-based triazole carbene complexes comprising specific ligands, their preparation and their use as catalysts in hydrogenation processes.

BACKGROUND OF THE INVENTION

In Ind. Eng. Chem. Res. 1991, 30, 1086-1092, Macromolecules 1992, 25, 883-886, J. Mol. Catal. A:Chem. 1998, 135, 121-132 and Rubber Chem. Technol. 2008, 81, 227-243 the Rhodium-based catalyst tris(triphenylphosphine)rhodium(I)chloride of formula (1) is disclosed for hydrogenation and hydrosilylation reactions of rubbers. However, high costs are associated with this catalyst which additionally requires the use of triphenylphosphine as co-catalyst. The catalyst degrades at 145° C.

(1)

In Chem. Comm. 1967, 305-306, Chem. Eur. J. 2010, 16, 12214-12220 and Tetrahedron Lett. 1966, 4871-4875 it is disclosed, that the complex tris(triphenylphosphine) hydrido ruthenium chloride of formula (2) can be used in a transfer hydrogenation for converting alkynes to alkenes. However, such catalyst does not efficiently hydrogenate nitrile rubbers and it is not selective for only olefins.

(2)

In J. Am. Chem. Soc. 1961, 83, 1262-1263, Chem. Eur. J. 2010, 16, 12214-12220, Am. Chem. Soc. 2010, 132, 16756-16758 and J. Mol. Catal. A:Chem. 2003, 206, 13-21 the catalyst of formula (3) as shown below is used as a transfer hydrogenation catalyst for alkynes to alkenes and for hydrogenation of amides to alcohols and amines under $H_2$. However, such a catalyst is not selective for olefins and contains a CO group.

(3)

In Organometallics 2006, 25, 99-110, Dalton Trans. 2008, 2603-2614, Organometallics 2009, 28, 1758-1775, Inorg. Chim Acta. 2010, 363, 625-632 and Organometallics, 2010, 29, 5450-5455 the catalyst of formula (4) as shown below is prepared from RuHCl(CO)(AsPh$_3$)$_3$ and IMes$_2$. Such preparation method, however, is not favorable due to the presence of AsPh$_3$. The catalyst further contains a CO group. Such catalyst is described for transfer hydrogenation of aromatic ketones with alcohols. It also hydrogenates olefins and ketones using $H_2$, however, it is not selective for olefins.

(4)

According to Organometallics 2004, 23, 86-94, the catalyst of formula (5) as shown below can be prepared from RuHCl(PPh$_3$)$_3$ and two equivalents of SIMes$_2$ with the formation of SIMes$_2$HCl as a by-product. However, no hydrogenation data is reported. It is not possible to displace PPh$_3$ with SIMes$_2$ without CH activation of the methyl groups.

(5)

In Dalton Trans., 2013, 42, 2362-2365 the catalyst of the formula (6) as shown below is prepared from [(p-cymene)RuCl$_2$]$_2$ and a triazolium salt with following treatment with K$_2$CO$_3$ in THF under reflux. However, no hydrogenation data is reported. A specific use for these 1,2,3-triazol-5-ylidene (tzNHC) ruthenium complexes is not disclosed in the paper.

(6)

Similar complexes with different metals and different ligands have been disclosed in the past.

In Dalton Trans., 2012, 41, 13074-13080 the catalyst of the formula (7) as shown below is prepared from IrCl$_2$(Cp*)(trz) (trz=triazolylidene) and sodium acetate under nitrogen. This iridium complex displays high potential as a water oxidation catalyst. The use as a hydrogenation catalyst is not disclosed. The use of other metals like ruthenium is also not suggested.

(7)

In Angew. Chem. Int. Ed. 2010, 49, 9765-9768 the catalyst of the formula (8) as shown below is prepared from [(Cp*IrCl$_2$)$_2$] (Cp*=C$_5$Me$_5$), Ag$_2$O and a pyridinium-functionalized triazolium salt. Iridium(III) cyclopentadienyl complexes are described to exhibit excellent activity in electrochemical induced water oxidation. However, no hydrogenation data is reported. Ruthenium-based complexes are neither disclosed nor suggested.

(8)

In Organometallics 2011, 30, 1689-1694 the catalyst of the formula (9) as shown below is prepared from Pd(OAc)$_2$ and a trans mono nuclear silver carbene complex [(Tz)$_2$Ag] (Tz=1,4-diphenyl-3-methyl-1,2,3-triazol-5-ylidene). However, no hydrogenation data is reported.

(9)

Summing up various complexes, which are used as catalysts, are already available for hydrogenation reactions. However, many of them contain unfavorable or expensive ligands, like PPh$_3$, form gels, are difficult to prepare, are not sufficiently active and/or selective.

Therefore, it was the object of the present invention to provide an inexpensive, thermally robust, gel formation inhibiting and olefin selective novel catalyst for hydrogenation reactions, particularly for hydrogenating polymers, and even more particularly for hydrogenating nitrile rubbers.

SUMMARY OF THE INVENTION

The above-mentioned objects have now been solved by providing novel ruthenium-based complexes according to general formula (I)

(I)

wherein

R is independently of one another hydrogen, hydroxy, thiol, thioether, ketone, aldehyde, ester, ether, amine, imine, amide, nitro, carboxylic acid, disulphide, carbonate, isocyanate, carbodiimide, carboalkoxy, carbamate, halogen, straight-chain or branched C$_1$-C$_{10}$-alkyl, preferably methyl, ethyl, n-propyl, iso-propyl, n-butyl, iso-butyl, sec-butyl or tert-butyl, C$_6$-C$_{24}$-aryl, preferably phenyl, or together with the carbon atoms to which they are bound form a C$_6$-C$_{10}$-cycloalkyl or C$_6$-C$_{10}$ aryl substituent, alkyl thiolate, aryl thiolate, B(R$^3$)$_2$ or B(R$^3$)$_3$, whereas R$^3$ is alkyl, aryl, alkoxy or aryloxy or CF$_3$, n is 0 to 4, preferably 0 to 2, more preferably 0 to 1

R$^1$ is straight-chain or branched C$_1$-C$_{10}$-alkyl, preferably methyl, ethyl, n-propyl, iso-propyl, n-butyl, iso-butyl, sec-butyl, tert-butyl, or neopentyl, C$_3$-C$_{10}$-cycloalkyl, preferably cyclohexyl or adamantyl, C$_6$-C$_{24}$-aryl, preferably phenyl, C$_1$-C$_{10}$-alkylsulphonate, preferably methanesulphonate, C$_6$-C$_{10}$-arylsulphonate, preferably p-toluenesulphonate, 2,4,6-trimethylphenyl (Mes) or 2,4,6-triisopropylphenyl (Trip), R$^2$ is hydrogen, straight-chain or branched C$_1$-C$_{10}$-alkyl, preferably methyl, ethyl, n-propyl, iso-propyl, n-butyl, iso-butyl, sec-butyl tert-butyl or neopentyl, C$_3$-C$_{10}$-cycloalkyl, preferably cyclohexyl or adamantyl, C$_6$-C$_{24}$-aryl, preferably phenyl, C$_1$-C$_{10}$-alkylsulphonate, preferably methanesulphonate, C$_6$-C$_{10}$-arylsulphonate, preferably p-toluenesulphonate, 2,4,6-trimethylphenyl (Mes) or 2,4,6-triisopropylphenyl (Trip), X is an anionic ligand, and Y$^1$ and Y$^2$ are identical or different and are each C$_1$-C$_{10}$-alkylphosphine or C$_3$-C$_{20}$-cycloalkylphosphine ligand, preferably tricyclohexylphosphine (PCy$_3$), a sulfonated C$_1$-C$_{10}$-alkylphosphine ligand, a C$_1$-C$_{10}$-alkylphosphinite ligand, a C$_1$-C$_{10}$-alkylphosphonite ligand, a C$_1$-C$_{10}$-alkyl phosphite ligand, a C$_1$-C$_{10}$-alkylarsine ligand, a C$_1$-C$_{10}$-alkylamine ligand, a substituted or not substituted pyridine ligand, a C$_1$-C$_{10}$-alkyl sulfoxide ligand, a C$_1$-C$_{10}$-alkyloxy ligand or a C$_1$-C$_{10}$-alkylamide ligand, each of which may be substituted by a phenyl group which may in turn be substituted by a halogen, C$_1$-C$_5$-alkyl or C$_1$-C$_5$-alkoxygroup.

DETAILED DESCRIPTION OF THE INVENTION

Figure 1:
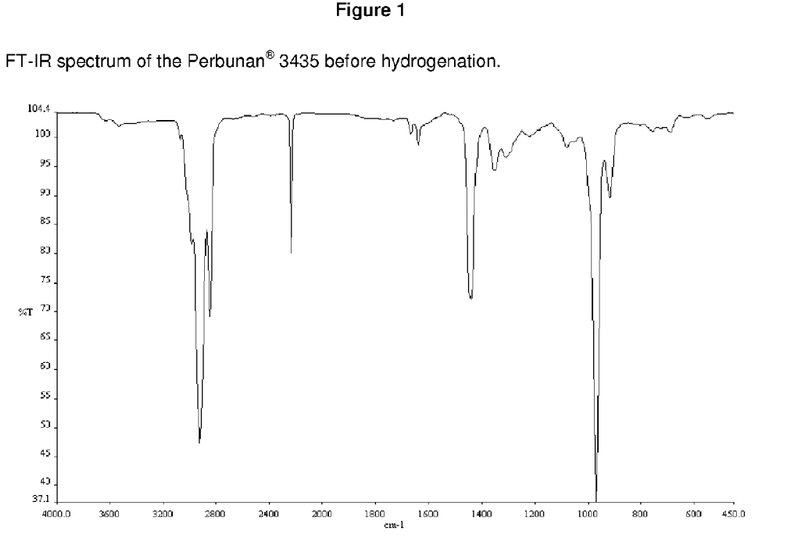
FIG. 1 shows an FT-IR spectrum of a nitrile rubber before hydrogenation.
Figure 2:
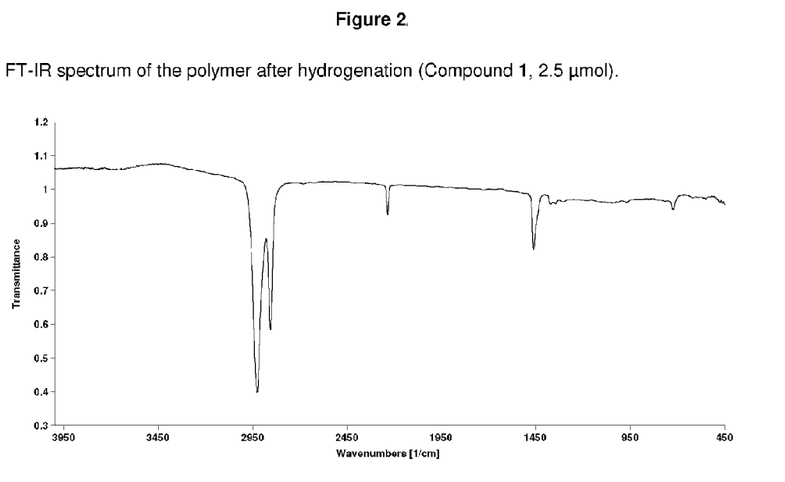
FIGS. 2 and 3 show FT-IR spectra of the nitrile rubber after hydrogenation in the presence of catalysts according to embodiments of the invention
Figure 3:
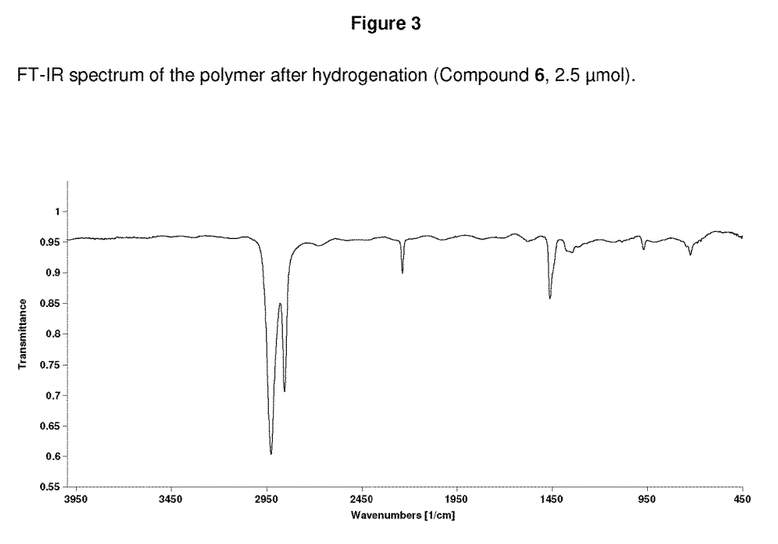

The novel ruthenium-based triazole carbene catalysts are excellently suited for hydrogenation reactions, are thermally robust, gel formation inhibiting, use less expensive ruthenium as transition metal and/or are selective for olefin hydrogenation.

Ligand Definition:

In the catalysts of the general formula (I), R is, independently of one another, hydrogen, hydroxy, thiol, thioether, ketone, aldehyde, ester, ether, amine, imine, amide, nitro, carboxylic acid, disulphide, carbonate, isocyanate, carbodiimide, carboalkoxy, carbamate, halogen, straight-chain or branched $C_1$-$C_{10}$-alkyl, preferably methyl, ethyl, n-propyl, iso-propyl, n-butyl, iso-butyl, sec-butyl or tert-butyl, $C_6$-$C_{24}$-aryl, preferably phenyl, or together with the carbon atoms to which they are bound form a $C_6$-$C_{10}$-cycloalkyl or $C_6$-$C_{10}$-aryl substituent, alkyl thiolate, aryl thiolate, $B(R^3)_2$ or $B(R^3)_3$, whereas $R^3$ is alkyl, aryl, alkoxy or aryloxy or $CF_3$.

All the above mentioned substituents as meanings of R can be substituted by one or more further substituents selected from the group consisting of straight-chain or branched $C_1$-$C_{10}$-alkyl, $C_3$-$C_8$-cycloalkyl, $C_1$-$C_{10}$-alkoxy, $C_6$-$C_{24}$-aryl and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen.

In the catalysts of the general formula (I), n is 0 to 4, preferably 0 to 2 and more preferably 0 to 1.

In the catalysts of the general formula (I), $R^1$ is straight-chain or branched $C_1$-$C_{10}$-alkyl, preferably methyl, ethyl, n-propyl, iso-propyl, n-butyl, iso-butyl, sec-butyl, tert-butyl or neopentyl, $C_3$-$C_{10}$-cycloalkyl, preferably cyclohexyl or adamantyl, $C_6$-$C_{24}$-aryl, preferably phenyl, $C_1$-$C_{10}$-alkylsulphonate, preferably methanesulphonate, $C_6$-$C_{10}$-arylsulphonate, preferably p-toluenesulphonate, 2,4,6-trimethylphenyl (Mes) or 2,4,6-triisopropylphenyl (Trip).

In the catalysts of the general formula (I), $R^2$ is hydrogen, straight-chain or branched $C_1$-$C_{10}$-alkyl, preferably methyl, ethyl, n-propyl, iso-propyl, n-butyl, iso-butyl, sec-butyl, tert-butyl or neopentyl, $C_3$-$C_{10}$-cycloalkyl, preferably cyclohexyl or adamantyl, $C_6$-$C_{24}$-aryl, preferably phenyl, $C_1$-$C_{10}$-alkylsulphonate, preferably methanesulphonate, $C_6$-$C_{10}$-arylsulphonate, preferably p-toluenesulphonate, 2,4,6-trimethylphenyl (Mes) or 2,4,6-triisopropylphenyl (Trip).

All the above mentioned substituents as meanings of $R^1$ and $R^2$ can be substituted by one or more further substituents selected from the group consisting of straight-chain or branched $C_1$-$C_{10}$-alkyl, in particular methyl, $C_3$-$C_8$-cycloalkyl, $C_1$-$C_5$-alkoxy, $C_6$-$C_{24}$-aryl and a functional group selected from the group consisting of hydroxy, thiol, thioether, ketone, aldehyde, ester, ether, amine, imine, amide, nitro, carboxylic acid, disulphide, carbonate, isocyanate, carbodiimide, carboalkoxy, carbamate and halogen.

In a preferred embodiment, $R^1$ and $R^2$ are identical or different and are each methyl, ethyl, n-propyl, iso-propyl, n-butyl, iso-butyl, sec-butyl, tert-butyl or, neopentyl, cyclohexyl, adamantyl, phenyl, $C_1$-methanesulphonate, p-toluenesulphonate, 2,4,6-trimethylphenyl (Mes) or 2,4,6-triisopropylphenyl (Trip).

In a more preferred embodiment, $R^1$ and $R^2$ are identical or different and are each methyl, ethyl, n-propyl, iso-propyl, n-butyl, iso-butyl, sec-butyl, tert-butyl or cyclohexyl, phenyl, 2,4,6-trimethylphenyl (Mes) or 2,4,6-triisopropylphenyl (Trip).

In a particularly preferred embodiment, $R^1$ is methyl.

In a particularly preferred embodiment, $R^2$ is phenyl, 2,4,6-trimethylphenyl (Mes) or 2,4,6-triisopropylphenyl (Trip).

In the catalysts of the general formula (I), X is an anionic ligand.

In a preferred embodiment, X is hydride, halide, pseudohalide, alkoxide, amide, triflate, phosphate, borate, straight-chain or branched $C_1$-$C_{30}$-alkyl or $C_6$-$C_{24}$-aryl, carboxylate, acetate, halogenated acetate, halogenated alkylsulfonate, tosylate or any weakly coordinating anionic ligands.

In a more preferred embodiment, X is hydride or halide preferably fluoride, chloride, bromide or iodide.

In a particularly preferred embodiment, X is chloride.

In the catalysts of the general formula (I), $Y^1$ and $Y^2$ are identical or different and are each a $C_1$-$C_{10}$-alkylphosphine ligand, $C_3$-$C_{20}$-cycloalkylphosphine ligand, preferably tricyclohexylphosphine ($PCy_3$), a sulfonated $C_1$-$C_{10}$-alkylphosphine ligand, a $C_1$-$C_{10}$-alkylphosphinite ligand, a $C_1$-$C_{10}$-alkylphosphonite ligand, a $C_1$-$C_{10}$-alkyl phosphite ligand, a $C_1$-$C_{10}$-alkylarsine ligand, a $C_1$-$C_{10}$-alkylamine ligand, a substituted or not substituted pyridine ligand, $C_1$-$C_{10}$-alkyl sulfoxide ligand, a $C_1$-$C_{10}$-alkyloxy ligand or a $C_1$-$C_{10}$-alkylamide ligand, each of which may be substituted by a phenyl group which may in turn be substituted by a halogen, $C_1$-$C_5$-alkyl or $C_1$-$C_5$-alkoxygroup.

The term "phosphine" includes, for example, $P(CF_3)_3$, $P(isopropyl)_3$, $P(CHCH_3(CH_2CH_3))_3$, $P(cyclopentyl)_3$, $P(cyclohexyl)_3$ and $P(neopentyl)_3$.

The term "phosphinite" includes, for example, cyclohexyl dicyclohexylphosphinite and isopropyl diisopropylphosphinite.

The term "phosphite" includes, for example, tricyclohexyl phosphite, tri-tert-butyl phosphite and triisopropyl phosphite.

The term "sulphonate" includes, for example, trifluoromethanesulphonate, tosylate and mesylate.

The term "sulfoxide" includes, for example, $(CH_3)_2S(=O)$ and $(C_6H_5)_2S=O$.

The term "thioether" includes, for example, $CH_3SCH_3$, $C_6H_5SCH_3$, $CH_3OCH_2CH_2SCH_3$ and tetrahydrothiophene.

Definition of Preferred Catalysts:

A preferred catalyst has the general formula (I) in which

R is independently of one another hydrogen, halogen, nitro, methyl, ethyl, n-propyl, iso-propyl, n-butyl, iso-butyl, sec-butyl or tert-butyl, phenyl, or together with the carbon atoms to which they are bound form a $C_6$-$C_{10}$-cycloalkyl or $C_6$-$C_{10}$-aryl substituent, alkyl thiolate, aryl thiolate, $B(R^3)_2$ or $B(R^3)_3$, whereas $R^3$ is alkyl, aryl, alkoxy or aryloxy or $CF_3$, n is 0 to 4, preferably 0 to 2, more preferably 0 to 1

$R^1$ and $R^2$ are identical or different and are each methyl, ethyl, n-propyl, iso-propyl, n-butyl, iso-butyl, sec-butyl, tert-butyl or neopentyl, cyclohexyl, adamantyl, phenyl, $C_1$-methanesulphonate, p-toluenesulphonate, 2,4,6-trimethylphenyl (Mes) or 2,4,6-triisopropylphenyl (Trip), X is hydride, halide, pseudohalide, alkoxide, amide, triflate, phosphate, borate, straight-chain or branched $C_1$-$C_{30}$-alkyl or $C_6$-$C_{24}$-aryl, carboxylate, acetate, halogenated acetate, halogenated alkylsulfonate, tosylate or any weakly coordinating anionic ligands, and $Y^1$ and $Y^2$ are identical or different and are each $C_1$-$C_{10}$-alkylphosphine or $C_3$-$C_{20}$-cycloalkylphosphine ligand, preferably tricyclohexylphosphine ($PCy_3$), a sulfonated $C_1$-$C_{10}$-alkylphosphine ligand, a $C_1$-$C_{10}$-alkylphosphinite ligand, a $C_1$-$C_{10}$-alkylphosphonite ligand, a $C_1$-$C_{10}$-alkyl phosphite ligand, a $C_1$-$C_{10}$-alkylarsine ligand, a $C_1$-$C_{10}$-alkylamine ligand, a substituted or not substituted pyridine ligand, a $C_1$-$C_{10}$-alkyl sulfoxide ligand, a $C_1$-$C_{10}$-alkyloxy ligand or a $C_1$-$C_{10}$-alkylamide ligand, each of which may be substituted by a phenyl group which may in turn be substituted by a halogen, $C_1$-$C_5$-alkyl or $C_1$-$C_5$-alkoxygroup.

A more preferred catalyst has the general formula (I) in which

R is independently of one another hydrogen, halogen, methyl, ethyl, n-propyl, iso-propyl, n-butyl, iso-butyl, sec-butyl or tert-butyl, phenyl, or together with the carbon atoms to which they are bound form a $C_6$-$C_{10}$-cycloalkyl or $C_6$-$C_{10}$-aryl substituent, or $CF_3$, n is 0 to 4, preferably 0 to 2, more preferably 0 to 1

$R^1$ and $R^2$ are identical or different and are each methyl, ethyl, n-propyl, iso-propyl, n-butyl, iso-butyl, sec-butyl, tert-butyl or cyclohexyl, phenyl, 2,4,6-trimethylphenyl (Mes) or 2,4,6-triisopropylphenyl (Trip), X is hydride or halide, preferably fluoride, chloride, bromide or iodide, and $Y^1$ and $Y^2$ are identical or different and are each $C_1$-$C_{10}$-alkylphosphine or $C_3$-$C_{20}$-cycloalkylphosphine ligand, preferably tricyclohexylphosphine ($PCy_3$), a sulfonated $C_1$-$C_{10}$-alkylphosphine ligand, a $C_1$-$C_{10}$-alkylphosphinite ligand, a $C_1$-$C_{10}$-alkylphosphonite ligand, a or $C_1$-$C_{10}$-alkyl phosphite ligand, a $C_1$-$C_{10}$-alkylarsine ligand, a $C_1$-$C_{10}$-alkylamine ligand, a substituted or not substituted pyridine ligand, a $C_1$-$C_{10}$-alkyl sulfoxide ligand, a $C_1$-$C_{10}$-alkyloxy ligand or a $C_1$-$C_{10}$-alkylamide ligand, each of which may be substituted by a phenyl group which may in turn be substituted by a halogen, $C_1$-$C_5$-alkyl or $C_1$-$C_5$-alkoxygroup.

An even more preferred catalyst has the general formula (I) in which

R is independently of one another hydrogen, methyl or $CF_3$, n is 0 to 4, preferably 0 to 2, more preferably 0 to 1

$R^1$ is methyl, $R^2$ is phenyl, 2,4,6-trimethylphenyl (Mes) or 2,4,6-triisopropylphenyl (Trip), X is chloride, and $Y^1$ and $Y^2$ are each tricyclohexylphosphine ($PCy_3$).

Synthesis of Catalysts:

In order to prepare the catalysts according to general formula (I) and all preferred, more preferred, even more preferred and particularly preferred catalysts, a person skilled in the art can use multistep procedures as outlined and exemplified in the experimental section of this application for various catalysts and can apply, generalize and modify to the extent necessary such described procedures to prepare catalysts falling under general formula (I). The preparation methods typically include schlenk or glovebox techniques. The characterization of the catalysts, substrates and compounds e.g. by $^1$H-, $^{13}$C-, $^{19}$F-, $^{31}$P-, or, or $^{11}$B-NMR, elemental analysis, and ESI-MS as outlined in the experimental section of this application are routine to a person skilled in the art of synthetic chemistry.

Typically, the catalyst according to formula (I) can be prepared by adding a solvent such as benzene or toluene to a mixture of substituted silver(I) triazolylidene and a ruthenium-complex such as $RuHCl(H_2)(PCy_3)_2$ or $RuHCl(PPh_3)_3$, which can be synthesized according to a modified literature procedure (M. Viciano, M. Feliz, R. Corberan, J. A. Mata, E. Clot and E. Pens, Organometallics, 2007, 26, 5304-5314.). The reaction mixture is than typically stirred at room temperature for about 40 to 50 hours. The catalyst can be typically purified by filtration, decantation or crystallization.

The present invention further relates to a process of hydrogenating substrates possessing at least one carbon-carbon double bond comprising subjecting said substrate to a hydrogenation reaction in the presence of a catalyst according to general formula (I).

Substrates to be Hydrogenated:

The process of the present invention is broadly applicable to the hydrogenation of a variety of substrates, including terminal olefins, internal olefins, cyclic olefins, conjugated olefins, and any further olefins having at least one carbon-carbon double bond and additionally at least one further polar unsaturated double or triple bond. The process is also applicable to the hydrogenation of polymers having carbon-carbon double bonds. Such polymers may represent homo-, co- or terpolymers.

As a terminal olefin or alkene, it is possible to hydrogenate a hydrocarbon compound with a terminal unsaturated carbon-carbon double bond having the general formula $C_nH_{2n}$. The terminal olefin can be a straight-chain or a branched hydrocarbon compound of any length, preferably 1-hexene.

As an internal olefin or alkene, it is possible to hydrogenate a hydrocarbon compound with an internal unsaturated carbon-carbon double bond having the general formula $C_nH_{2n}$. The internal olefin can be a straight-chain or a branched hydrocarbon of any length, and may be 2-hexene.

As a cyclic olefin or cycloalkene, it is possible to hydrogenate a hydrocarbon compound with a cyclic unsaturated carbon-carbon double bond having the general formula $C_nH_{2n-2}$. The cyclic olefin can be a ring of any size, and may be cyclohexene.

As a conjugated olefin or dialkene, it is possible to hydrogenate a hydrocarbon compound with conjugated carbon-carbon unsaturated double bonds. The conjugation can be a straight-chain or a branched hydrocarbon of any length, preferably styrene.

As an olefin, it is also possible to selectively hydrogenate a hydrocarbon compound with at least one unsaturated carbon-carbon double bond and at least one other unsaturated polar double or triple bond. Such unsaturated polar bonds are surprisingly left unaltered. The carbon-carbon double bond in such olefins can be of any nature including terminal, internal, cyclic and conjugated ones. The additional unsaturated polar bond can be of any nature with preference given to carbon-nitrogen, carbon-phosphorus, carbon-oxygen, and carbon-sulfur unsaturated polar bonds.

Polymers having carbon-carbon double bonds may also be subjected to the inventive process. Such polymers preferably comprise repeating units based on at least one conjugated diene monomer.

The conjugated diene can be of any nature. In one embodiment $C_4$-$C_6$-conjugated dienes are used. Preference is given to 1,3-butadiene, isoprene, 1-methylbutadiene, 2,3-dimethylbutadiene, piperylene, chloroprene, or mixtures thereof. More preference is given to 1,3-butadiene, isoprene or mixtures thereof. Particular preference is given to 1,3-butadiene.

In a further embodiment polymers having carbon-carbon double bonds may be subjected to the inventive process which comprise repeating units of not only at least one conjugated diene as monomer (a) but additionally at least one further copolymerizable monomer (b).

Examples of suitable monomers (b) are olefins, such as ethylene or propylene.

Further examples of suitable monomers (b) are vinylaromatic monomers, such as styrene, α-methyl styrene, o-chlorostyrene or vinyltoluenes, vinylesters of aliphatic or branched $C_1$-$C_{18}$-monocarboxylic acids, such as vinyl acetate, vinyl propionate, vinyl butyrate, vinyl valerate, vinyl hexanoate, vinyl 2-ethylhexanoate, vinyl decanoate, vinyl laurate and vinyl stearate.

A preferred polymer to be used in the present invention is a copolymer of 1,3-butadiene and styrene or α-methylstyrene. Said copolymers may have a random or block type structure.

Further examples of suitable monomers (b) are esters of ethylenically unsaturated monocarboxylic acids or mono- or diesters of dicarboxylic acids with generally $C_1$-$C_{12}$-alkanols, e.g. esters of acrylic acid, methacrylic acid, maleic acid, fumaric acid and itaconic acid with e.g. methanol, ethanol, n-propanol, isopropanol, 1-butanol, 2-butanol, isobutanol, tert.-butanol, n-hexanol, 2-ethylhexanol, or $C_5$-$C_{10}$-cycloalkanols, such as cyclopentanol or cyclohexanol, and of these preferably the esters of acrylic and/or methacrylic acid, examples being methyl methacrylate, n-butyl methacrylate, tert-butyl methacrylate, n-butyl acrylate, tert-butyl acrylate, and 2-ethylhexyl acrylate.

The inventive process may be further used to hydrogenate so-called nitrile rubbers. Nitrile rubbers ("NBR") represent copolymers or terpolymers comprising repeating units of at least one conjugated diene and at least one α,β-unsaturated nitrile monomer, or copolymers or terpolymers comprising repeating units of at least one conjugated diene and at least one α,β-unsaturated nitrile monomer and one or more further copolymerizable monomers.

The conjugated diene in such nitrile rubbers can be of any nature. Preference is given to using $C_4$-$C_6$-conjugated dienes. Particular preference is given to 1,3-butadiene, isoprene, 2,3-dimethylbutadiene, piperylene or mixtures thereof. In particular, use is preferably made of 1,3-butadiene or isoprene or mixtures thereof. Very particular preference is given to 1,3-butadiene.

As α,β-unsaturated nitrile monomer, it is possible to use any known α,β-unsaturated nitrile, with preference being given to $C_3$-$C_5$-α,β-unsaturated nitriles such as acrylonitrile, methacrylonitrile, ethacrylonitrile or mixtures thereof. Particularly preference is given to acrylonitrile.

A particularly preferred nitrile rubber to be subjected to hydrogenation according to the invention is thus a copolymer of acrylonitrile and 1,3-butadiene.

In addition to the conjugated diene and the α,β-unsaturated nitrile, it is possible to use one or more further copolymerizable monomers known to those skilled in the art, e.g. termonomers containing carboxyl groups, like α,β-unsaturated monocarboxylic acids, their esters or amides, α,β-unsaturated dicarboxylic acids, their monoesters or diesters, or their corresponding anhydrides or amides.

As α,β-unsaturated monocarboxylic acids it is possible to use acrylic acid and methacrylic acid.

It is also possible to employ esters of the α,β-unsaturated monocarboxylic acids, preferably their alkyl esters and alkoxyalkyl esters. Preference is given to the alkyl esters, especially $C_1$-$C_{18}$-alkyl esters, of the α,β-unsaturated monocarboxylic acids. Particular preference is given to alkyl esters, especially $C_1$-$C_{18}$-alkyl esters, of acrylic acid or of methacrylic acid, more particularly methyl acrylate, ethyl acrylate, propyl acrylate, n-butyl acrylate, tert-butyl acrylate, 2-ethylhexyl acrylate, n-dodecyl acrylate, methyl methacrylate, ethyl methacrylates, butyl methacrylate and 2-ethylhexyl methacrylate. Also preferred are alkoxyalkyl esters of the α,β-unsaturated monocarboxylic acids, more preferably alkoxyalkyl esters of acrylic acid or of methacrylic acid, more particular $C_2$-$C_{12}$-alkoxyalkyl esters of acrylic acid or of methacrylic acid, very preferably methoxymethyl acrylate, methoxyethyl (meth)acrylate, ethoxyethyl (meth)acrylate and methoxyethyl (meth)acrylate. Use may also be made of mixtures of alkyl esters, such as those mentioned above, for example, with alkoxyalkyl esters, in the form of those mentioned above, for example. Use may also be made of cyanoalkyl acrylate and cyanoalkyl methacrylates in which the C atom number of the cyanoalkyl group is 2-12, preferably α-cyanoethyl acrylate, β-cyanoethyl acrylate and cyanobutyl methacrylate. Use may also be made of hydroxyalkyl acrylates and hydroxyalkyl methacrylate in which the C atom number of the hydroxyalkyl groups is 1-12, preferably 2-hydroxyethyl acrylate, 2-hydroxyethyl methacrylate and 3-hydroxypropyl acrylate; use may also be made of fluorine-substituted benzyl-group-containing acrylates or methacrylates, preferably fluorobenzyl acrylate, and fluorobenzyl methacrylate. Use may also be made of acrylates and methacrylates containing fluoroalkyl groups, preferably trifluoroethyl acrylate and tetrafluoropropyl methacrylate. Use may also be made of α,β-unsaturated carboxylic esters containing amino groups, such as dimethylaminomethyl acrylate and diethylaminoethyl acrylate.

As copolymerizable monomers it is possible, furthermore, to use α,β-unsaturated dicarboxylic acids, preferably maleic acid, fumaric acid, crotonic acid, itaconic acid, citraconic acid and mesaconic acid.

Use may be made, furthermore, of α,β-unsaturated dicarboxylic anhydrides, preferably maleic anhydride, itaconic anhydride, citraconic anhydride and mesaconic anhydride.

It is possible, furthermore, to use monoesters or diesters of α,β-unsaturated dicarboxylic acids.

These α,β-unsaturated dicarboxylic monoesters or diesters may be, for example, alkyl esters, preferably $C_1$-$C_{10}$-alkyl, more particularly ethyl, n-propyl, iso-propyl, n-butyl, tert-butyl, n-pentyl or n-hexyl esters, alkoxyalkyl esters, preferably $C_2$-$C_{12}$-alkoxyalkyl, more preferably $C_3$-$C_8$-alkoxyalkyl, hydroxyalkyl, preferably $C_1$-$C_{12}$-hydroxyalkyl, more preferably $C_2$-$C_8$-hydroxyalkyl, cycloalkyl esters, preferably $C_5$-$C_{12}$-cycloalkyl, more preferably $C_8$-$C_{12}$-cycloalkyl, alkylcycloalkyl esters, preferably $C_8$-$C_{12}$-alkylcycloalkyl, more preferably $C_7$-$C_{10}$-alkylcycloalkyl, aryl esters, preferably $C_8$-$C_{14}$-aryl esters, these esters being monoesters or diesters, and it also being possible, in the case of the diesters, for the esters to be mixed esters.

Particularly preferred alkyl esters of α,β-unsaturated monocarboxylic acids are methyl (meth)acrylate, ethyl (meth)acrylate, propyl (meth)acrylate, n-butyl (meth)acrylate, t-butyl (meth)acrylate, hexyl (meth)acrylate, 2-ethylhexyl (meth)acrylate, octyl (meth)acrylate, 2-propylheptyl acrylate and lauryl (meth)acrylate. More particularly, n-butyl acrylate is used.

Particularly preferred alkoxyalkyl esters of the α,β-unsaturated monocarboxylic acids are methoxyethyl (meth)acrylate, ethoxyethyl (meth)acrylate and methoxyethyl (meth)acrylate. More particularly, methoxyethyl acrylate is used.

Particularly preferred hydroxyalkyl esters of the α,β-unsaturated monocarboxylic acids are hydroxyethyl (meth)acrylate, hydroxypropyl (meth)acrylate and hydroxybutyl (meth)acrylate.

Other esters of the α,β-unsaturated monocarboxylic acids that are used are additionally, for example, polyethylene glycol (meth)acrylate, polypropylene glycol (meth)acrylate, glycidyl (meth)acrylate, epoxy (meth)acrylate, N-(2-hydroxyethyl)acrylamides, N-(2-hydroxy-methyl)acrylamides and urethane (meth)acrylate.

Examples of α,β-Unsaturated Dicarboxylic Monoesters Encompass

- maleic acid monoalkyl esters, preferably monomethyl maleate, monoethyl maleate, monopropyl maleate and mono-n-butyl maleate;
- maleic acid monocycloalkyl esters, preferably monocyclopentyl maleate, monocyclohexyl maleate and monocycloheptyl maleate;
- maleic acid monoalkyl cycloalkyl esters, preferably monomethyl cyclopentyl maleate and monoethyl cyclohexyl maleate;
- maleic acid monoaryl esters, preferably monophenyl maleate;
- maleic acid monobenzyl esters, preferably monobenzyl maleate;
- fumaric acid monoalkyl esters, preferably monomethyl fumarate, monoethyl fumarate, monopropyl fumarate and mono-n-butyl fumarate;
- fumaric acid monocycloalkyl esters, preferably monocyclopentyl fumarate, monocyclohexyl fumarate and monocycloheptyl fumarate;
- fumaric acid monoalkyl cycloalkyl esters, preferably monomethyl cyclopentyl fumarate and monoethyl cyclohexyl fumarate;
- fumaric acid monoaryl esters, preferably monophenyl fumarate;
- fumaric acid monobenzyl esters, preferably monobenzyl fumarate;
- citraconic acid monoalkyl esters, preferably monomethyl citraconate, monoethyl citraconate, monopropyl citraconate and mono-n-butyl citraconate;
- citraconic acid monocycloalkyl esters, preferably monocyclopentyl citraconate, monocyclohexyl citraconate and monocycloheptyl citraconate;
- citraconic acid monoalkyl cycloalkyl esters, preferably monomethyl cyclopentyl citraconate and monoethyl cyclohexyl citraconate;
- citraconic acid monoaryl esters, preferably monophenyl citraconate;
- citraconic acid monobenzyl esters, preferably monobenzyl citraconate;
- itaconic acid monoalkyl esters, preferably monomethyl itaconate, monoethyl itaconate, monopropyl itaconate and mono-n-butyl itaconate;
- itaconic acid monocycloalkyl esters, preferably monocyclopentyl itaconate, monocyclohexyl itaconate and monocycloheptyl itaconate;
- itaconic acid monoalkyl cycloalkyl esters, preferably monomethyl cyclopentyl itaconate and monoethyl cyclohexyl itaconate;
- itaconic acid monoaryl esters, preferably monophenyl itaconate;
- itaconic acid monobenzyl esters, preferably monobenzyl itaconate;
- mesaconic acid monoalkyl esters, preferably mesaconic acid monoethyl esters;

As α,β-unsaturated dicarboxylic diesters it is possible to use the analogous diesters based on the abovementioned monoester groups, and the ester groups may also be chemically different groups.

Preferably the substrate to be hydrogenated is a nitrile rubber comprising repeating units of at least one conjugated diene and at least one α,β-unsaturated nitrile monomer, or a nitrile rubber comprising at least one conjugated diene and at least one α,β-unsaturated nitrile monomer and one or more further copolymerizable monomers, preferably a nitrile rubber comprising repeating units of at least one conjugated diene selected from the group consisting of 1,3-butadiene, isoprene, 2,3-dimethylbutadiene, piperylene and mixtures thereof, at least one α,β-unsaturated nitrile selected from the group consisting of acrylonitrile, methacrylonitrile, ethacrylonitrile and mixtures thereof, and of no or one or more further copolymerizable monomers selected from the group consisting of α,β-unsaturated monocarboxylic, dicarboxylic acids, their esters or amides.

The proportions of conjugated diene and α,β-unsaturated nitrile monomer in the NBR polymers to be used can vary within wide ranges. The proportion of the conjugated diene or the sum of conjugated dienes is usually in the range from 40% to 90% by weight, preferably in the range from 50% to 85% by weight, based on the total polymer. The proportion of the α,β-unsaturated nitrile or the sum of the α,β-unsaturated nitriles is usually from 10% to 60% by weight, preferably from 15% to 50% by weight, based on the total polymer. The proportions of the monomers in each case add up to 100% by weight. The additional monomers can be present in amounts of from 0% to 40% by weight, preferably from 0.1% to 40% by weight, particularly preferably from 1% to 30% by weight, based on the total polymer. In this case, corresponding proportions of the conjugated diene or dienes and/or the α,β-unsaturated nitrile or nitriles are replaced by the proportions of the additional monomers, with the proportions of all monomers in each case adding up to 100% by weight.

The preparation of such nitrile rubbers by polymerization of the abovementioned monomers is adequately known to those skilled in the art and is comprehensively described in the literature (e.g. Houben-Weyl, Methoden der Organischen Chemie Bd.14/1, 30 Georg Thieme Verlag Stuttgart 1961; Rompp Lexikon der Chemie, Band 2, 10. Auflage 1997; P. A. Lovell, M. S. El-Aasser, Emulsion Polymerization and Emulsion Polymers, John Wiley & Sons, ISBN: 0471 967467; H. Gerrens, Fortschr. Hochpolym. Forsch. 1, 234 (1959)).

Nitrile rubbers which can be used for the purposes of the invention are also commercially available, e.g. as products marketed under the trademarks Perbunan® and Krynac® by Lanxess Deutschland GmbH.

The nitrile rubbers which can be used for the hydrogenation have a Mooney viscosity (ML 1+4 at 100° C.) in the range from 30 to 70, preferably from 30 to 50. This corresponds to a weight average molecular weight $M_w$ in the range from 150,000 to 500,000, preferably in the range from 180,000 to 400,000. The nitrile rubbers used typically have a polydispersity PDI=$M_w/M_n$ ($M_n$ is the number average molecular weight) in the range of 2.0-6.0 and preferably in the range 2.0-4.0.

The determination of the Mooney viscosity is carried out in accordance with ASTM standard D 1646.

Hydrogenated nitrile rubbers obtained pursuant to this invention can have a Mooney viscosity (ML 1+4 at 100° C.) in the range of greater than 0 up to 150, typically the Mooney viscosity lies in the range of from 5 to 150, preferably of from 10 to 120, more preferably of from 30 to 110, even more preferably of from 35 to 100, and particularly preferably of from 50 to 100 and most preferably of from 60 to 90.

They typically have a polydispersity PDI=$M_w/M_n$, where $M_w$ is the weight average molecular weight and $M_n$ is the number average molecular weight, in the range of 1.5 to 6 and preferably in the range of 1.8 to 4.

Hydrogenation Conditions:

The process of the present invention is generally carried out at a temperature in the range from 0° C. to 200° C., preferably in the range from 15° C. to 150° C. This means that the process may be carried out at mild conditions. In case low molecular weight olefins like terminal olefins, internal olefins, cyclic olefins, conjugated olefins, or any other olefins having at least one carbon-carbon double bond and additionally at least one further polar unsaturated double bond are subjected to hydrogenation, the temperature typically lies in the range from 20° C. to 100° C. In case polymers with double bonds in the polymer backbone are used as substrates the hydrogenation temperature typically lies in a range from 40° C. to 200° C., preferably in the range from 70° C. to 150° C.

The hydrogenation process of the present invention is preferably carried out with hydrogen gas at a pressure from 0.1 MPa to 20 MPa, preferably at a pressure from 1 MPa to 16 MPa. In one embodiment of the present process said hydrogen gas is essentially pure.

Preferably the hydrogenation process is carried out at a temperature in the range from 0° C. to 200° C. with hydrogen gas at a pressure from 0.1 MPa to 20 MPa, preferably at a temperature in the range from 15° C. to 150° C. with hydrogen gas at a pressure from 1 MPa to 16 MPa.

The amount of catalyst according to general formula (I) can vary in a broad range. Typically the catalyst according to general formula (I) is used in a molar ratio from (0.01-0.20):1, preferably from (0.01-0.05):1 based on the substrate to be hydrogenated.

In the hydrogenation of rubber polymers the amount of catalyst according to formula (I) may also vary in a broad range. The amount of catalyst is then calculated on a weight base ratio in "phr" (parts per hundred rubber). Typically 0.005 phr to 2.5 phr catalyst are used based on the rubber. Preferably 0.01 phr to 2 phr and more preferably 0.025 phr to 2 phr catalyst are used based on the rubber.

The hydrogenation can be carried out in a suitable solvent which does not deactivate the catalyst used and also does not adversely affect the reaction in any other way. Preferred solvents include but are not restricted to methanol, chlorobenzene, bromobenzene, dichloromethane, benzene, toluene, methyl ethyl ketone, acetone, tetrahydrofuran, tetrahydropyran, dioxane and cyclohexane. The particularly preferred solvent is chlorobenzene. In some cases, when the substrate to be hydrogenated itself can function as solvent, e.g. in the case of 1-hexene, the addition of a further additional solvent can also be omitted.

According to the present invention the catalyst can be introduced into the polymer by any possible means, such as e.g. mechanical mixing, preferably by using a procedure which can result in a homogeneous distribution of the catalyst and polymer.

In one embodiment of the present invention the catalyst according to formula (I) is contacted with the substrate to be hydrogenated by adding the catalyst or catalyst solution to a substrate solution and mixing until an efficient distribution and dissolution of the catalyst has taken place.

The present process can be performed in the presence or absence of any further co-catalyst or other additives. It is not necessary to add such further co-catalyst or other additives. This applies in particular to co-catalysts which are typically used e.g. in combination with other hydrogenation catalysts known from prior art like the Wilkinson's catalyst. In one embodiment of the present invention the process is conducted in the presence or absence of co-catalysts having the formula $R^1_m Z$, wherein $R^1$ are identical or different and are each a $C_1$-$C_8$-alkyl group, a $C_4$-$C_8$-cycloalkyl group, a $C_6$-$C_{15}$-aryl group or a $C_7$-$C_{15}$-aralkyl group, Z is phosphorus, arsenic, sulphur or a sulphoxide group S=O, preferably phosphorus, and m is 2 or 3, preferably 3. In a further embodiment the present process is conducted in the presence or absence of triphenylphosphine.

The hydrogenation process of the present invention can be undertaken in a suitable reactor equipped with temperature regulating and agitating means. It is possible to perform the process either batch-wise or continuously.

During the course of the hydrogenation reaction of the present invention, the hydrogen is added to the reactor. The reaction time is typically from about one quarter of an hour to about 100 hours, depending on operational conditions. As the novel catalysts are robust, it is not necessary to use a special gas dryer to dry the hydrogen.

According to the present invention, when the hydrogenation reaction is complete, to the extent desired, the reaction vessel can be cooled, if applicable, and vented and the hydrogenated substrate can be isolated by conventional methods well known to any artisan.

During the process according to the invention it may happen that a hydrogenation reaction and a metathesis reaction occur simultaneously. In case polymeric substrates, and in particular nitrile rubbers, are used as substrates in the process according to the invention, such metathesis reaction results in a decrease of the molecular weight of the substrate.

The novel ruthenium-based triazole carbene complexes can be used as catalysts for the hydrogenation of unsaturated compounds comprising carbon-carbon double bonds, preferably nitrile rubber.

Such complex catalysts are inexpensive, thermally robust, gel formation inhibiting and olefin selective.

EXAMPLES

In the following "PPh$_3$" is used as an abbreviation of triphenylphosphine, "Ph" means in each case phenyl, "Mes" represents in each case 2,4,6-trimethylphenyl, "Trip" is used as an abbreviation of 2,4,6-triisopropylphenyl, "iPr$_3$" is used as an abbreviation of triisopropyl and "PCy$_3$" is used as an abbreviation of tricyclohexylphosphine.

General Procedures:

Manipulations were done using standard Schlenk and glovebox techniques (O$_2$ level <0.1 ppm; N$_2$ as inert gas), unless noted differently. Solvents, namely CH$_2$Cl$_2$, Et$_2$O, THF, toluene, and hexane, were used in dried form and stored under N$_2$. RuHCl(PPh$_3$)$_3$ and RuHCl(H$_2$)(PCy$_3$)$_2$ were prepared according to a modified literature procedure (M. Viciano, M. Feliz, R. Corberan, J. A. Mata, E. Clot and E. Pens, Organometallics, 2007, 26, 5304-5314.).

A Synthesis of Ligands and Catalysts

1

Synthesis of 1.

Benzene (10 mL) was added to a mixture of [(C$_6$H$_2$iPr$_3$)CH$_2$C$_2$N$_2$(NMe)Ph)$_2$Ag][AgCl$_2$] (0.261 g, 0.25 mmol) and RuHCl(H$_2$)(PCy$_3$)$_2$ (0.350 g, 0.50 mmol). The reaction mixture was stirred at room temperature for 48 hours resulting in a red solution with brown precipitate. The brown solid was filtered off. All volatiles were removed from the red solution resulting in a red solid which was washed with hexane (3×10 mL). The solid was dried under high vacuum to give 1 as pure product (0.351 g). The hexane phase was allowed to rest for 48 hours during which time red crystals formed (0.058 g) as pure product 1. The solids were combined and dried thoroughly to give 1 (0.409 g, 76%).

Compound 1:

$^1$H-NMR (CD$_2$Cl$_2$): δ 0.92-2.16 (m, 84H, PCy$_3$ and CH$_3$ of iPr), 2.97 (sept, J=6.9 Hz, 1H, CH of iPr), 3.07 (sept, J=6.9 Hz, 2H, CH of iPr), 4.11 (s, 3H, N—CH$_3$), 5.58 (s, 2H, CH$_2$), 6.51 (t, J=7.7 Hz, 1H, C$_6$H$_4$), 6.60 (t, J=7.2 Hz, 1H, C$_6$H$_4$), 7.08 (d, J=7.5 Hz, 1H, C$_6$H$_4$), 7.18 (s, 2H, C$_6$H$_2$), 8.25 (d, J=8.0 Hz, 1H, C$_6$H$_4$).

$^{13}$C-NMR (CD$_2$Cl$_2$): δ 24.12, 26.99, 28.05, 28.33, 28.59, 30.69, 30.97, 31.53, 34.70, 37.09, 38.20 (PCy$_3$, CH and CH$_3$ of iPr), 49.28 (N—CH$_3$), 66.06 (CH$_2$), 117.52, 118.91, 122.03, 122.34, 125.50, 139.91, 143.65, 149.44, 150.04, 154.62 (Ar—C), 181.59 (Ru—C).

$^{31}$P-NMR (CD$_2$Cl$_2$): δ 24.49.

Anal. Calcd for C$_{61}$H$_{98}$ClN$_3$P$_2$Ru (1071.92): C, 68.35; H, 9.22; N, 3.92.

Found: C, 68.22; H, 9.21; N, 3.87.

3

Synthesis of 2 and 3.

Benzene (10 mL) was added to a mixture of [(C$_6$H$_6$)CH$_2$C$_2$N$_2$(NMe)Ph)$_2$Ag][AgCl$_2$] (0.197 g, 0.25 mmol) and RuHCl(H$_2$)(PCy$_3$)$_2$ (0.350 g, 0.50 mmol). The reaction mixture was stirred at room temperature for 48 hours resulting in a red solution with brown precipitate. The brown solid was filtered off. The red solution was concentrated to ca. 2-3 mL and added dropwise to hexane (15 mL) while stirring vigorously. This resulted in a red solution with orange precipitate. The solid was filtered off and dried under high vacuum to give 2 (0.291 g, ca. 60%) (compound 2 contains impurities and could not be isolated in pure form). The red solution was allowed to rest 18 hours at room temperature resulting in an orange semicrystalline precipitate and red solution. The red solution was left at −35° C. for 48 hours resulting in red crystals. The crystals were dried to give pure 3 (0.038 g, 8%).

Synthesis of 4 and 5.

Benzene (10 mL) was added to a mixture of [(C$_6$H$_2$Me$_3$)CH$_2$C$_2$N$_2$(NMe)Ph)$_2$Ag][AgCl$_2$] (0.230 g, 0.25 mmol) and RuHCl(H$_2$)(PCy$_3$)$_2$ (0.350 g, 0.50 mmol). The reaction mixture was stirred at room temperature for 48 hours resulting in a red solution with brown precipitate. The brown solid was filtered off. The red solution was concentrated to ca. 2-3 mL and added dropwise to hexane (15 mL) while stirring vigorously. This resulted in a red solution with orange precipitate. The solid was filtered off and dried under high vacuum to give 4 (0.281 g, 56%) as crude product. Crystallization from toluene gave pure 4 (0.202 g, 40%) as red crystals. The red solution was allowed to rest 18 hours at room temperature resulting in an orange semicrystalline precipitate and red solution. The red solution was left at −35° C. for 48 hours resulting in red crystals. The crystals were dried to give pure 5 (0.038 g, 8%).

Compound 4:

$^1$H-NMR (CD$_2$Cl$_2$): δ 1.08-2.23 (m, 66H, PCy$_3$), 2.30 (s, 3H, CH$_3$), 2.41 (s, 6H, CH$_3$), 4.23 (s, 3H, N—CH$_3$), 5.96 (s, 2H, CH$_2$), 6.98 (m, 1H, C$_6$H$_4$), 7.52-7.79 (m, 4H, C$_6$H$_2$ and C$_6$H$_4$), 9.01 (m, 1H, C$_6$H$_4$).

$^{13}$C-NMR (CD$_2$Cl$_2$): δ 20.15, 21.18, 24.35, 27.14, 28.28, 29.42, 30.24, 30.64, 32.32, 33.22, 38.19, 39.26 (PCy$_3$ and CH$_3$), 49.04 (N—CH$_3$), 62.86 (CH$_2$), 122.37, 125.36, 128.64, 129.35, 129.81, 130.04, 132.28, 139.16, 140.65, 143.54 (Ar—C), 178.51 (Ru—C).

$^{31}$P-NMR (CD$_2$Cl$_2$): δ 23.96.

Anal. Calcd for C$_{55}$H$_{86}$ClN$_3$P$_2$Ru (987.76): C, 66.88; H, 8.78; N, 4.25.

Found: C, 66.81; H, 8.91; N, 4.26.

Synthesis of 6 and 7.

Benzene (10 mL) was added to a mixture of [((C$_6$H$_2$Me$_3$)CH$_2$C$_2$N$_2$(NMe)(C$_6$H$_4$Me))$_2$Ag][AgCl$_2$] (0.216 g, 0.26 mmol) and RuHCl(H$_2$)(PCy$_3$)$_2$ (0.350 g, 0.50 mmol). The reaction mixture was stirred at room temperature for 48 hours resulting in a red solution with brown precipitate. The brown solid was filtered off. The red solution was concentrated to ca. 2-3 mL and added dropwise to hexane (15 mL) while stirring vigorously. This resulted in a red solution with orange-red precipitate. The solid was filtered off and dried under high vacuum to give 6 as crude product. The crude product was dissolved in toluene and crystallization gave red crystals as pure 6 (0.213 g, 42%). The red solution was allowed to rest 48 hours at room temperature resulting in red crystals. The crystals were dried and $^1$H-NMR measurement suggested that the red crystals were a mixture of 6 and 7. Compound 7 could not be isolated in pure.

Compound 6:

$^1$H-NMR (CD$_2$Cl$_2$): δ 0.89-2.05 (m, 66H, PCy$_3$), 2.24 (s, 3H, CH$_3$), 4.17 (s, 3H, N—CH$_3$), 5.81 (s, 2H, CH$_2$), 6.48 (d, J=7.6 Hz, 1H, C$_6$H$_3$), 7.06 (d, J=7.6 Hz, 1H, C$_6$H$_3$), 7.31-7.42 (m, 5H, C$_6$H$_5$), 7.96 (s, 1H, C$_6$H$_3$).

$^{13}$C-NMR (CD$_2$Cl$_2$): δ 21.78, 22.75, 27.08, 28.44, 30.31, 30.44, 30.63, 33.28, 34.54, 36.84, 37.12 (PCy$_3$, CH$_3$ and N—CH$_3$), 56.20 (CH$_2$), 118.82, 118.94, 127.84, 127.98, 128.69, 132.61, 136.51, 137.11, 143.38, 154.31 (Ar—C), 183.11, 183.96 (Ru—C).

$^{31}$P-NMR (CD$_2$Cl$_2$): δ 24.17.

Anal. Calcd for C$_{53}$H$_{82}$ClN$_3$P$_2$Ru (959.71): C, 66.33; H, 8.61; N, 4.38.

Found: C, 66.25; H, 8.56; N, 4.42.

Synthesis of 8 and 9.

Benzene (10 mL) was added to a mixture of [((C$_6$H$_2$Me$_3$)CH$_2$C$_2$N$_2$(NMe)(C$_6$H$_4$CF$_3$))$_2$Ag][AgCl$_2$] (0.244 g, 0.26 mmol) and RuHCl(H$_2$)(PCy$_3$)$_2$ (0.350 g, 0.50 mmol). The reaction mixture was stirred at room temperature for 48 hours resulting in a red solution with brown precipitate. The brown solid was filtered off. The red solution was concentrated to ca. 2-3 mL and added dropwise to hexane (15 mL) while stirring vigorously. This resulted in a red solution with orange-red precipitate. The solid was filtered off and dried under high vacuum to give 8 as crude product. The crude product was dissolved in toluene and crystallization gave red crystals as pure 8 (0.193 g, 38%). The red solution was allowed to rest 48 hours at room temperature resulting in red crystals. The crystals were dried and $^1$H-NMR measurement suggested that the red crystals were a mixture of 8 and 9. Compound 9 could not be isolated in pure form.

Compound 8:
$^1$H-NMR (CD$_2$Cl$_2$): δ 0.83-2.04 (m, 66H, PCy$_3$), 4.25 (s, 3H, N—CH$_3$), 5.85 (s, 2H, CH$_2$), 6.91 (d, J=7.5 Hz, 1H, C$_6$H$_3$), 7.23 (d, J=7.5 Hz, 1H, C$_6$H$_3$), 7.31-7.44 (m, 5H, C$_6$H$_5$), 8.43 (s, 1H, C$_6$H$_3$).
$^{13}$C-NMR (CD$_2$Cl$_2$): δ 26.98, 28.28, 28.31, 28.36, 30.48, 30.53, 36.70, 36.76, 36.82, 37.54 (PCy$_3$ and N—CH$_3$), 56.37 (CH$_2$), 114.08, 118.42, 127.95, 128.81, 129.67, 130.34, 136.04, 138.53, 143.40, 153.15 (Ar—C and CF$_3$), 184.81, 186.88 (Ru—C).
$^{31}$P-NMR (CD$_2$Cl$_2$): δ 23.58.
Anal. Calcd for C$_{53}$H$_{79}$ClN$_3$P$_2$Ru (1013.68): C, 62.80; H, 7.86; N, 4.15.
Found: C, 62.87; H, 7.83; N, 4.18.

Synthesis of 10.

Toluene (30 mL) was added to a mixture of [(C$_6$H$_2$iPr$_3$)CH$_2$C$_2$N$_2$(NMe)Ph)$_2$Ag][AgCl$_2$] (0.520 g, 0.50 mmol) and RuHCl(PPh$_3$)$_3$ (0.926 g, 1.00 mmol). The reaction mixture was stirred at room temperature for 40 hours resulting in a dark red solution with brown precipitate. The precipitate was filtered off and the solution was concentrated to ca. one fourth to its original volume. The concentrated solution was added dropwise to well stirred hexanes (30 mL) resulting in a red precipitate with pale red solution. The liquid was syringed off and the solid was washed with hexanes (3×10 mL). Pure product as dark red crystals were deposited from the pale red solution on standing. The red solid was dried to give crude product. The crude product was dissolved in toluene and crystallization gave second batch of dark red crystals as pure 10 (0.383 g, 37%). Occasionally colorless crystals of AgCl(PPh$_3$) were also crystallized out and separated from the dark red crystals mechanically.

Compound 10:
$^1$H-NMR (CD$_2$Cl$_2$): δ 0.93 (d, J=6.3 Hz, 12H, CH$_3$ of iPr), 1.26 (d, J=6.5 Hz, 6H, CH$_3$ of iPr), 2.28 (sept, J=6.3 Hz, 1H, CH of iPr), 2.89 (sept, J=6.3 Hz, 2H, CH of iPr), 3.30 (s, 3H, Me), 5.22 (s, 2H, CH$_2$), 6.17 (d, J=8.6 Hz, 1H, Ar—H), 6.40-6.45 (m, 2H, Ar—H), 7.01 (s, 2H, Ar—H), 7.05-7.42 (m, 30H, PPh$_3$), 7.91 (d, J=8.6 Hz, 1H, Ar—H).
$^{13}$C-NMR (CD$_2$Cl$_2$): δ 24.04 (CH$_3$ of iPr), 24.98 (CH of iPr), 30.30 (CH$_3$ of iPr), 34.60 (CH of Pr), 36.49 (N—CH$_3$), 48.98 (CH$_2$), 118.75, 120.46, 121.85, 122.94, 124.38, 127.66, 128.70, 140.07, 149.56, 149.91, 154.64 (Ar—C), 174.27, 175.45 (Ru—C).
$^{31}$P-NMR (CD$_2$Cl$_2$): δ 39.95.
Anal. Calcd for C$_{61}$H$_{62}$ClN$_3$P$_2$Ru (1035.64): C, 70.74; H, 6.03; N, 4.06.
Found: C, 71.01; H, 5.99; N, 4.09.

Synthesis of 11 and 12.

Toluene (30 mL) was added to a mixture of [(O$_6$H$_5$)CH$_2$C$_2$N$_2$(NMe)Ph)$_2$Ag][AgCl$_2$] (0.396 g, 0.50 mmol) and RuHCl(PPh$_3$)$_3$ (0.926 g, 1.00 mmol). The reaction mixture was stirred at room temperature for 40 hours resulting in a dark red solution with brown precipitate. The precipitate was filtered off and the solution was concentrated to ca. one fourth to its original volume. The concentrated solution was added dropwise to well stirred hexanes (30 mL) resulting in a red-orange precipitate with pale red solution. The red solution was syringed off and dark red crystals were obtained on standing for 2 days. The crystals were dried under high vacuum to give pure 12 (0.046 g, 5%). The red-orange solid was washed with hexanes (3×10 mL) and dried to give crude product 11. The crude product was dissolved in $CH_2Cl_2$ (3 mL) and slow diffusion of $Et_2O$ over 10 days gave dark red crystals as pure 11 (0.191 g, 21%).

Compound 11:

$^1$H-NMR ($CD_2Cl_2$): δ 3.34 (s, 3H, Me), 4.86 (s, 2H, $CH_2$), 6.29-6.36 (m, 1H, Ar—H), 6.41-6.49 (m, 2H, Ar—H), 6.80 (d, J=7.6 Hz, 2H, Ar—H), 6.95-7.03 (m, 3H, Ar—H), 7.09-7.45 (m, 30H, $PPh_3$), 8.08 (d, J=7.5 Hz, 1H, Ar—H).

$^{13}$C-NMR ($CD_2Cl_2$): δ 36.59 (N—$CH_3$), 55.99 ($CH_2$), 118.83, 120.08, 122.96, 124.38, 127.73, 128.70, 129.35, 134.48, 134.79, 135.09, 136.01, 139.77, 141.09, 153.53 (Ar—C), 173.39, 180.64 (Ru—C).

$^{31}$P-NMR ($CD_2Cl_2$): δ 37.70.

Anal. Calcd for $C_{52}H_{44}ClN_3P_2Ru$ (909.40): C, 68.68; H, 4.88; N, 4.62.

Found: C, 68.73; H, 4.85; N, 4.60.

B.1 Hydrogenation of NBR $C_6H_5Cl$ was distilled over $P_2O_5$. $H_2$ was purified by passing through a Matheson gas drier model 450B.

In Series 1 and 2 commercially available Perbunan® T 3435 was used as nitrile rubber:

Perbunan® T 3435: 34 wt % ACN; Mooney viscosity (ML 1+4 at 100° C.): 35+/−3 MU; $M_n$=80,000 g/mol; $M_w$=260,000 g/mol.

In the glove box, the Parr reactor was charged with 5.0 mL of NBR solution (5 wt.-% in $C_6H_5Cl$) and catalyst 1, 3, 4, 5, 6, 8, 10, 11 or 12 respectively (2.5 mg, ca. 2.5 μmol and 1.0 mg, ca. 1.0 μmol). The reactor was taken out of the glove box and purged with 20 bar $H_2$ (four times). The temperature was set at 80° C. and the pressure at 40 bar of $H_2$. After the temperature was equilibrated to 80° C., the pressure was increased to 50 bar and the reaction was carried out for 20 hours while stirring vigorously. The hydrogenation was stopped by cooling down the reactor to room temperature and venting $H_2$. The polymer was characterized by FT-IR (thin film on KBr plates).

B.2 Hydrogenation of 1-hexene

In a glove box, a sample of the metal complex 10 (0.005 g, 5 μmol) or 11 (0.005 g, 5 μmol) or 12 (0.005 g, 5 μmol), deuterated solvent (0.5 mL) ($C_6D_6$ for 12 and $CD_2Cl_2$ for 10 and 11) and substrate i.e. 1-hexene (0.1 mmol) were combined in a vial. The mixture was transferred to a J. Young tube and the J. Young tube was sealed. On a Schlenk line, the reaction mixture was degassed four times using the freeze-pump-thaw method. The sample was then frozen once more in liquid nitrogen and 4.053 bar of $H_2$ was added. The J. Young tube was sealed again and warmed to room temperature and then placed in an oil bath pre-heated to 45° C. $^1$H-NMR spectra were measured at appropriate intervals and relative integration of substrate and product peaks were used to determine the composition of the mixture.

B.3 Hydrogenation of Styrene

Identical procedure as in B.2 was followed.

B.4 Hydrogenation of Phenylacetylene

Identical procedure as in B.2 was followed.

B.5 Hydrogenation of Acrylaldehyde

Identical procedure as in B.2 was followed.

B.6 Hydrogenation of Acrylonitrile

Identical procedure as in B.2 was followed.

B.7 Hydrogenation of 3-buten-2-One

Identical procedure as in B.2 was followed.

B.8 Hydrogenation of Allylamine

Identical procedure as in B.2 was followed.

B.9 Hydrogenation of 1-vinylimidazole

Identical procedure as in B.2 was followed.

TABLE 1

Hydrogenation of NBR (Perbunan ® T3435) (80° C.; 50 bar; 20 h).

| | | Catalyst | | | | HNBR (hydrogenated nitrile rubber) | | |
|---|---|---|---|---|---|---|---|---|
| | No. | molar mass [g/mol] | loading [μmol] | [mg] | NBR [g] | degree of hydrogenation [%] | Mn [g/mol] | Mw [g/mol] | PDI |
| IE | 1 | 1,071.92 | 2.5 | 2.7 | 0.55 | ~100 | 97.364 | 232.181 | 2.38 |
| IE | 1 | 1,071.92 | 1 | 1.1 | 0.55 | ~95 | 52.739 | 100.303 | 1.90 |
| IE | 2 | 945.68 | 2.5 | 2.4 | 0.55 | ~95 | 74.040 | 158.170 | 2.14 |
| IE | 2 | 945.68 | 1 | 1.0 | 0.55 | ~90 | 39.467 | 101.758 | 2.58 |
| IE | 3 | 947.70 | 2.5 | 2.4 | 0.55 | ~95 | 110.927 | 217.663 | 1.96 |
| IE | 3 | 947.70 | 1 | 1.0 | 0.55 | ~90 | 61.491 | 139.988 | 2.28 |
| IE | 4 | 987.76 | 2.5 | 2.5 | 0.55 | ~95 | 55.417 | 152.882 | 2.76 |
| IE | 4 | 987.76 | 1 | 1 | 0.55 | ~90 | 37.534 | 100.500 | 2.68 |
| IE | 5 | 989.78 | 2.5 | 2.5 | 0.55 | ~95 | 93.650 | 174.899 | 1.86 |
| IE | 5 | 989.78 | 1 | 1 | 0.55 | ~90 | 89.473 | 170.973 | 1.91 |
| IE | 6 | 989.71 | 2.5 | 2.5 | 0.55 | ~100 | 105.641 | 194.436 | 1.84 |
| IE | 6 | 989.71 | 1 | 1 | 0.55 | ~100 | 49.874 | 97.546 | 1.96 |
| IE | 8 | 1,013.68 | 2.5 | 2.5 | 0.55 | ~100 | 104.476 | 201.100 | 1.92 |
| IE | 8 | 1,013.68 | 1 | 1 | 0.55 | ~95 | 45.431 | 89.506 | 1.97 |
| CE | 10 | 1,035.64 | 2.5 | 2.5 | 0.55 | No conversion | nd | nd | nd |
| CE | 10 | 1,035.64 | 1 | 1 | 0.55 | No conversion | nd | nd | nd |
| CE | 11 | 909.40 | 2.5 | 2.3 | 0.55 | No conversion | nd | nd | nd |
| CE | 11 | 909.40 | 1 | 1 | 0.55 | No conversion | nd | nd | nd |

TABLE 1-continued

Hydrogenation of NBR (Perbunan ® T3435) (80° C.; 50 bar; 20 h).

| | Catalyst | | | | | HNBR (hydrogenated nitrile rubber) | | |
|---|---|---|---|---|---|---|---|---|
| | | molar mass | loading | NBR | degree of hydrogenation | Mn | Mw | |
| | No. | [g/mol] | [µmol] | [mg] | [%] | [g/mol] | [g/mol] | PDI |
| CE | 12 | 911.41 | 2.5 | 2.3 | 0.55 | No conversion | nd | nd | nd |
| CE | 12 | 911.41 | 1 | 1 | 0.55 | No conversion | nd | nd | nd | nd = not determinable;
IE = inventive example;
CE = comparative example
The use of complexes of general formula (I) comprising arylphosphine ligands such as triphenylphosphine ligands prevents the hydrogenation of unsaturated polymers like NBR.

TABLE 2

Hydrogenation of alkenes with catalysts 10, 11 and 12$^a$.

| Substrate | product | No. | t/yield (h,/%)$^b$ | No. | t/yield (h,/%)$^b$ | No. | t/yield (h,/%)$^b$ |
|---|---|---|---|---|---|---|---|
| 1-hexene | hexane | 10 | 4/100 | 11 | 6/100 | 12 | 6/100 |
| styrene | ethylbenzene | 10 | 8/100 | 11 | 14/100 | 12 | 16/100 |
| phenylacetylene | ethylbenzene | 10 | 8/100 | 11 | 24/100 | 12 | 24/96$^c$ |
| acrylaldehyde | propionaldehyde | 10 | 3/100 | 11 | 8/100 | 12 | 12/100 |
| acrylonitrile | propionitrile | 10 | 22/100 | 11 | 24/100 | 12 | 24/86 |
| 3-buten-2-one | 2-butanone | 10 | 16/100 | 11 | 18/100 | 12 | 20/100 |
| allylamine | propylamine | 10 | 8/100 | 11 | 14/100 | 12 | 16/100 |
| 1-vinylimidazole | 1-ethylimidazole | 10 | 12/100 | 11 | 24/86 | 12 | 24/71 |

$^a$Conditions: 0.10 mmol of substrate and 5 mol % of catalyst in CD$_2$Cl$_2$ or C$_6$D$_6$ at 45° C. under 4 bar of H$_2$.
$^b$Yields were determined by $^1$H-NMR spectroscopy.
$^c$4% of the product was observed to be styrene.

The complexes 10, 11 and 12 show hydrogenation of small molecules like 1-hexane, styrene, phenylacetylene, acrylaldehyde, acrylonitrile, 3-buten-2-one, allylamine and 1-vinylimidazole.

The invention claimed is:

1. A ruthenium-based complex catalyst according to general formula (I)

wherein
R is independently of one another hydrogen, hydroxy, thiol, thioether, ketone, aldehyde, ester, ether, amine, imine, amide, nitro, carboxylic acid, disulphide, carbonate, Isocyanate, carbodilmide, carboalkoxy, carbamate, halogen, straight-chain or branched C$_1$-C$_{10}$-alkyl, C$_6$-C$_{24}$-aryl, or together with the carbon atoms to which they are bound form a C$_6$-C$_{10}$-cycloalkyl or C$_6$-C$_{10}$-aryl substituent, alkyl thiolate, aryl thiolate, B(R$^3$)$_2$ or B(R$^3$)$_3$, whereas R$^3$ is alkyl, aryl, alkoxy or aryloxy or CF$_3$,
n is 0 to 4, R$^1$ is straight-chain or branched C$_1$-C$_{10}$-alkyl, C$_3$-C$_{10}$-cycloalkyl, C$_6$-C$_{24}$-aryl, C$_1$-C$_{10}$-alkylsulphonate, or C$_6$-C$_{10}$-arylsulphonate,
R$^2$ is hydrogen, straight-chain or branched C$_1$-C$_{10}$-alkyl, C$_3$-C$_{10}$-cycloalkyl, C$_6$-C$_{24}$-aryl, C$_1$-C$_{10}$-alkylsulphonate, C$_6$-C$_{10}$-arylsulphonate,
X is an anionic ligand, and
Y$^1$ and Y$^2$ are identical or different and are each a C$_1$-C$_{10}$-alkylphosphine ligand, C$_3$-C$_{20}$-cycloalkylphosphine ligand, a sulfonated C$_1$-C$_{10}$-alkylphosphine ligand, a C$_1$-C$_{10}$-alkylphosphinite ligand, a C$_1$-C$_{10}$-alkylphosphonite ligand, a C$_1$-C$_{10}$-alkyl phosphite ligand, a C$_1$-C$_{10}$-alkylarsine ligand, a C$_1$-C$_{10}$-alkylamine ligand, a substituted or not substituted pyridine ligand, a C$_1$-C$_{10}$-alkyl sulfoxide ligand, a C$_1$-C$_{10}$-alkyloxy ligand or a C$_1$-C$_{10}$-alkylamide ligand, each of which may be substituted by a phenyl group which may in turn be substituted by a halogen, C$_1$-C$_5$-alkyl or C$_1$-C$_5$-alkoxy group.

2. The catalyst according to claim 1, wherein:
R is independently of one another hydrogen, halogen, nitro, methyl, ethyl, n-propyl, iso-propyl, n-butyl, iso-butyl, sec-butyl or tert-butyl, phenyl, or together with the carbon atoms to which they are bound form a C$_6$-C$_{10}$-cycloalkyl or C$_6$-C$_{10}$-aryl substituent, alkyl thiolate, aryl thiolate, B(R$^3$)$_2$ or B(R$^{3)}$)$_3$, whereas R$^3$ is alkyl, aryl, alkoxy or aryloxy or CF$_3$,
N is 0 to 4,
R$^1$ and R$^2$ are identical or different and are each methyl, ethyl, n-propyl, iso-propyl, n-butyl, iso-butyl, sec-butyl, tert-butyl or neopentyl, cyclohexyl, adamantyl, phenyl, methanesulphonate, p-toluenesulphonate, 2,4, 6-trimethylphenyl (Mes) or 2,4,6-triisopropylphenyl (Trip), X is hydride, halide, pseudohalide, alkoxide, amide, triflate, phosphate, borate, straight-chain or branched $C_1$-$C_{30}$-alkyl or $C_6$-$C_{24}$-aryl, carboxylate, acetate, halogenated acetate, halogenated alkylsulfonate, tosylate or any weakly coordinating anionic ligands, and $Y^1$ and $Y^2$ are identical or different and are each $C_1$-$C_{10}$-alkylphosphine or $C_3$-$C_{20}$-cycloalkylphosphine ligand, a sulfonated $C_1$-$C_{10}$-alkylphosphine ligand, a $C_1$-$C_{10}$-alkylphosphinite ligand, a $C_1$-$C_{10}$-alkylphosphonite ligand, a ,$C_1$-$C_{10}$-alkyl phosphite ligand, a $C_1$-$C_{10}$-alkylarsine ligand, a $C_1$-$C_{10}$-alkylamine ligand, a substituted or not substituted pyridine ligand, a $C_1$-$C_{10}$-alkyl sulfoxide ligand, a $C_1$-$C_{10}$-alkyloxy ligand or a $C_1$-$C_{10}$-alkylamide ligand, each of which may be substituted by a phenyl group which may in turn be substituted by a halogen, $C_1$-$C_5$-alkyl or $C_1$-$C_5$-alkoxy group.

3. The catalyst according to claim 1, wherein:

R is independently of one another, hydrogen, halogen, methyl, ethyl, n-propyl, iso-propyl, n-butyl, iso-butyl, sec-butyl or tert-butyl, phenyl, or together with the carbon atoms to which they are bound form a $C_6$-$C_{10}$-cycloalkyl or $C_6$-$C_{10}$-atyl substituent, or $CF_3$, n is 0 to 4, $R^1$ and $R^2$ are identical or different and are each methyl, ethyl, n-propyl, iso-propyl, n-butyl, iso-butyl, sec-butyl or tert-butyl, cyclohexyl, phenyl, 2,4,6-trimethylphenyl (Mes) or 2,4,6 triisopropylphenyl (Trip), X is hydride or halide, $Y^1$ and $Y^2$ are identical or different and are each $C_1$-$C_{10}$-alkylphosphine or $C_3$-$C_{20}$-cycloalkylphosphine ligand, a sulfonated $C_1$-$C_{10}$-alkylphosphine ligand, a $C_1$-$C_{10}$-alkylphosphinite ligand, a $C_1$-$C_{10}$-alkylphosphonite ligand, a $C_1$-$C_{10}$-alkyl phosphite ligand, a $C_1$-$C_{10}$-alkylarsine ligand, a $C_1$-$C_{10}$-alkylamine ligand, a substituted or not substituted pyridine ligand, a $C_1$-$C_{10}$--alkyl sulfoxide ligand, a $C_1$-$C_{10}$-alkyloxy ligand or a $C_1$-$C_{10}$-alkylamide ligand, each of which may be substituted by a phenyl group which may in turn be substituted by a halogen, $C_1$-$C_5$-alkyl or $C_1$-$C_5$-alkoxy group.

4. A ruthenium-based complex catalyst according to general formula (I)

wherein:

R is independently of one another, hydrogen, methyl or $CF_3$, n is 0 to 4, $R^1$ is methyl, $R^2$ is phenyl, 2,4,6-trimethylphenyl (Mes) or 2,4,6-triisopropylphenyl (Trip), X is chloride, and $Y^1$ and $Y^2$ are each tricyclohexylphosphine ($PCy_3$).

5. A process for hydrogenating substrates possessing at least one carbon-carbon double bond, the process comprising subjecting a substrate possessing at least one carbon-carbon double bond to a hydrogenation reaction in the presence of the catalyst according to claim 1.

6. The process according to claim 5, wherein the substrate to be hydrogenated is selected from the group consisting of terminal olefins, internal olefins, cyclic olefins, conjugated olefins, any further olefins having at least one carbon-carbon double bond and additionally at least one further polar unsaturated double or triple bond and polymers having carbon-carbon double bonds.

7. The process according to claim 5, wherein the substrate is selected from the group consisting of: hydrocarbon compounds with a terminal unsaturated carbon-carbon double bond having the general formula $C_nH_{2n}$; hydrocarbon compounds with an internal unsaturated carbon-carbon double bond having the general formula $C_nH_{2n}$; cyclic hydrocarbon compounds with an unsaturated carbon-carbon double bond having a general formula $C_nH_{2n-2}$, hydrocarbon compounds with at least two conjugated unsaturated carbon-carbon double bonds; and olefins having a unsaturated carbon-carbon double bond in the presence of at least one other unsaturated polar bond.

8. The process according to claim 5, wherein the substrate is a polymer having carbon-carbon double bonds, and the polymer comprises repeating units based on at least one conjugated diene monomer.

9. The process according to claim 8, wherein the substrate is:

a nitrile rubber comprising repeating units of at least one conjugated dime and at least one α,β-unsaturated nitrite monomer, or a nitrile rubber comprising repeating units of at least one conjugated diene and at least one α,β-unsaturated nitrile monomer and one or more further copolymerizable monomers.

10. The process according to claim 5, wherein the hydrogenation is carried out at a temperature of 0° C. to 200° C. with hydrogen gas at a pressure of 0.1 MPa to 20 MPa.

11. The process according to claim 5, wherein the catalyst according to general formula (I) is used in a molar ratio of (0.01-0.20):1 based on the substrate to be hydrogenated.

12. The process according to claim 5, wherein the catalyst according to general formula (I) is used in a ratio of 0.005 phr to 2.5 phr catalyst based on the susbstrate wherein the substrate is a rubber polymer.

13. The catalyst according to claim 4, wherein:

R is it of one another hydrogen, methyl or $CF_3$,

N is 0 to 1, $R^1$ is methyl, $R^2$ is phenyl, 2,4,6-trimethylphenyl (Mes), or 2,4,6-triisopropylphenyl (Trip), X is chloride, and $Y^1$ and $Y^2$ are each tricyclohexylphosphine ($PCy_3$).

14. The catalyst according to claim 3, wherein:

n is 0 to 2;

X is hydride, fluoride, chloride, bromide or iodide, and for $Y^1$ and $Y^2$, the $C_3$-$C_{20}$-cycloalkylphosphine ligand is tricyclohexylphosphine ($PCy_3$).

15. The process according to claim 7, wherein the substrate is selected from the group consisting of: straight chain or branched hydrocarbon compounds with a terminal unsaturated carbon-carbon double bond having the general formula $C_nH_{2n}$;straight-chain or branched hydrocarbon compounds with an internal unsaturated carbon-carbon double bond having the general formula $C_nH_{2n}$; cyclic hydrocarbon compounds with an unsaturated carbon-carbon double bond having a general formula $C_nH_{2n-2}$; straight-chain or branched hydrocarbon compounds with at least two conjugated unsaturated carbon-carbon double bonds; and olefins having at least one terminal, internal, cyclic or conjugated carbon-carbon double bond and at least one further unsaturated polar bond.

16. The process according to claim 15, wherein the substrate is selected from the group consisting of: 1-hexene; 2-hexene; cyclohexene; styrene; and olefins with at least one terminal, internal, cyclic or conjugated carbon-carbon double bond and at least one further unsaturated polar bond selected from carbon-nitrogen, carbon-phosphorus, carbon-oxygen, and carbon-sulfur unsaturated polar bonds.

17. The process according to claim 9, wherein the substrate is a nitrile rubber comprising repeating units of;
   at least one conjugated diene selected from the group consisting of 1,3-butadiene, isoprene, 2,3-dimethylbutadiene, piperylene and mixtures thereof,
   at least one α,β-unsaturated nitrile selected from the group consisting of acrylonitrile, methacrylonitrile, ethacrylonitrile and mixtures thereof, and
   of no or one or more further copolymerizabie monomers selected from the group consisting of α,β-unsaturated monocarboxylic or dicarboxylic acids, their esters or amides.

18. The process according to claim 10, wherein the hydrogenation is carded out at a temperature of 15° C. to 150° C. with hydrogen gas at a pressure of 1 MPa to 16 MPa.

19. The process according to claim 11, wherein the catalyst according to general formula (I) is used in a molar ratio of (0.01-0.05):1 based on the substrate to be hydrogenated.

20. The process according to claim 12, wherein the catalyst according to general formula (I) is used in a ratio of 0.025 phr to 2 phr catalyst based on the substrate.

\* \* \* \* \*